United States Patent [19]

Schulte et al.

[11] Patent Number: 4,560,375

[45] Date of Patent: Dec. 24, 1985

[54] FLOW CONTROL VALVE

[75] Inventors: Rudolf R. Schulte; Gary P. East, both of Santa Barbara; Marga M. Bryant; Alfons Heindl, both of Goleta, all of Calif.

[73] Assignee: Pudenz-Schulte Medical Research Corp., Santa Barbara, Calif.

[21] Appl. No.: 575,165

[22] Filed: Jan. 30, 1984

Related U.S. Application Data

[63] Continuation-in-part of Ser. No. 510,381, Jun. 30, 1983, abandoned, which is a continuation of Ser. No. 208,514, Nov. 20, 1980, abandoned.

[51] Int. Cl.$^4$ .............................................. A61M 5/00
[52] U.S. Cl. ........................................... 604/9; 604/8
[58] Field of Search ..................................... 604/8–10; 137/522

[56] References Cited

U.S. PATENT DOCUMENTS

| | | |
|---|---|---|
| 2,867,213 | 1/1959 | Thomas . |
| 2,933,102 | 4/1960 | Hillman et al. . |
| 3,111,125 | 11/1963 | Schulte . |
| 3,288,142 | 11/1966 | Hakim . |
| 3,492,996 | 2/1970 | Fountain . |
| 3,503,402 | 3/1970 | Schulte . |
| 3,527,226 | 9/1970 | Hakim . |
| 3,595,240 | 7/1971 | Mishler . |
| 3,601,128 | 8/1971 | Hakim . |
| 3,756,243 | 9/1973 | Schulte . |
| 3,758,073 | 9/1973 | Schulte . |
| 3,768,508 | 10/1973 | Schulte . |
| 3,769,982 | 11/1973 | Schulte . |
| 3,827,439 | 8/1974 | Schulte et al. . |
| 3,851,588 | 12/1974 | Taylor . |
| 3,980,097 | 9/1976 | Ellis . |
| 4,084,606 | 4/1978 | Mittleman . |
| 4,364,395 | 12/1982 | Redmond et al. . |
| 4,475,899 | 10/1984 | Muller ................................. 604/9 |

OTHER PUBLICATIONS

Brochure: The Surgical Treatment of Hydrocephalus-An Historical Review, Date: 1/1/81, Author: Robert H. Pudenz, M.D.
Brochure: Silastic Hydrocephalus Shunt, Date: 12/72, Author: Dow Corning.
Brochure: Holter-Hausner International.
Brochure: Accu-Flow Valve System-Hydrocephalus Shunt Systems, Copright: 1981, Author: Codman.

Primary Examiner—C. Fred Rosenbaum
Assistant Examiner—Gene B. Kartchner
Attorney, Agent, or Firm—Fulwider, Patton, Rieber, Lee & Utecht

[57] ABSTRACT

A surgically implantable flow control valve is provided for use in shunt systems for controlling the release of entrapped body fluids. The valve includes a relatively rigid, unitized molded plastic base separating an inlet chamber from an outlet chamber and including one or more apertures passing from the inlet chamber to the outlet chamber, and a resilient membrane which is molded of a material different from the material of the plastic base and which is secured to the base in a manner covering the apertures through the base on the outlet chamber side of the base. Fluid flow occluders on the base facilitate both proximal and distal flushing, and radiopaque indicators and markers permit a surgeon to ascertain specific information about the device and the functioning of the shunt system which would otherwise be unavailable without additional surgery.

43 Claims, 5 Drawing Figures

U.S. Patent    Dec. 24, 1985    Sheet 2 of 2    4,560,375
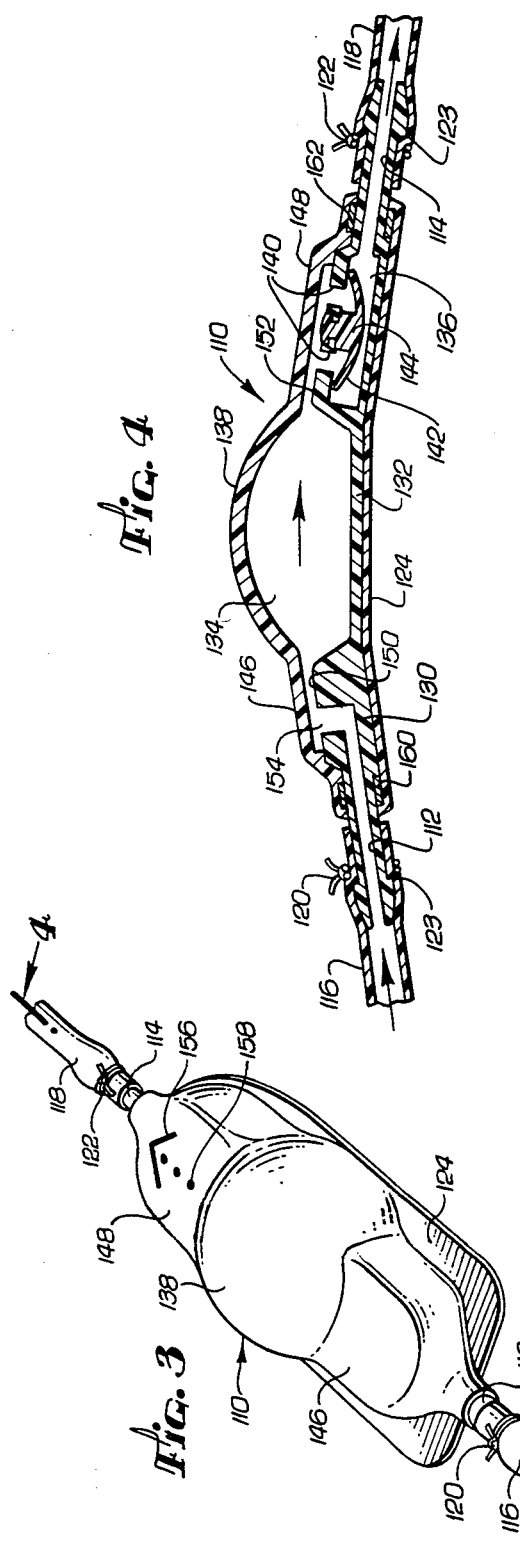
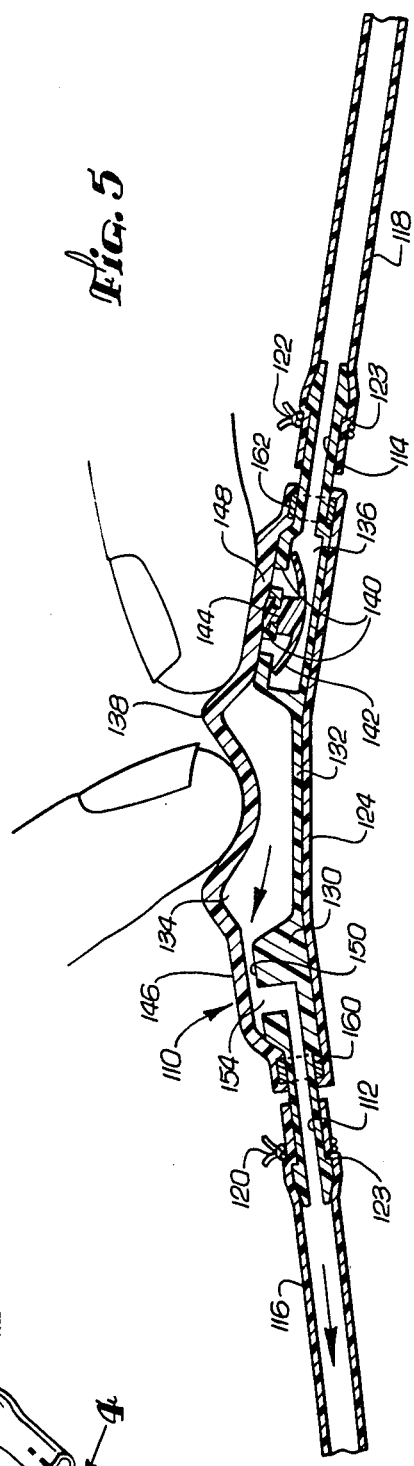

FLOW CONTROL VALVE

RELATED APPLICATIONS

This is a continuation-in-part of application Ser. No. 510,381, filed June 30, 1983, now abandoned which is a continuation of application Ser. No. 208,514, which was filed Nov. 20, 1980, and is now abandoned.

BACKGROUND OF THE INVENTION

This invention relates generally to surgically implantable valves, and more particularly, to one-way flow control valves for controlling the flow of cerebrospinal fluid out of a brain ventricle and preventing backflow of fluid into the brain ventricle.

As is well known in the medical arts, to relieve undesirable accumulation of fluids, it is frequently necessary to provide a means for draining a fluid from one part of the human body to another in a controlled manner. This is required, for example, in the treatment of hydrocephalus, an ailment usually afflicting infants or children in which fluids which ought to drain away accumulate within the skull and thereby exert extreme pressure and skull deforming forces.

In treating hydrocephalus, cerebrospinal fluid accumulated in the brain ventricles is drained away by a catheter inserted into the ventricle through the skull, and the catheter is connected to a tube which conducts the fluid away from the brain to be reintroduced into the vascular system, as by extending through the patient's jugular vein to the atrium portion of the heart. To control the flow of cerebrospinal fluid and maintain the proper pressure in the brain ventricle, a pump or valve is placed in the conduit between the brain and the heart atrium.

Many such devices have been used heretofore, but prior devices have tended to become obstructed by particulate matter entering the drainage system or by the backward diffusion of blood into the system. Further, some prior devices have included moving parts which tended to adhere to other parts of the device and become immobile. When this occurs, the device itself becomes a barrier in the drainage system, and it adds to the problem it is intended to solve.

Moreover, manufacturers have been faced with a dilemma regarding the use of metal components in such valves. Some prior devices have included metal components which tended to interfere with X-ray photography and produce radiation scatter ("sunburst effect") on films taken by computerized axial tomography (CAT) scanning equipment, and such X-ray photography and CAT scanning frequently accompanies the use of surgically implanted flow control valves. However, it is desirable in some instances to be able to ascertain specific information from an implanted device by X-ray photography without having to reopen the patient's skin. For instance, it would be very desirable to provide X-ray detectable means for designating the proximal-to-distal flow path of the implanted device. Additionally, an X-ray detectable marker which would facilitate detection of a separation of drainage tubing from the valve could be very useful to an attending physician where doubt exists as to the integrity of an implanted shunt system.

Accordingly, there has been a long existing need in the medical arts for a convenient and effective device for controlling the flow of fluid from one part of the human body to another, which device is relatively inexpensive to manufacture and which can be constructed substantially of non-metallic parts which are not subject to adhering to one another and causing malfunction of the device. Such a device would preferably include proximal-to-distal flow indicators as well as markers facilitating the detection of a drainage tubing disconnect, such markers and indicators being detectable by X-ray photography. As will become apparent from the following description, the present invention satisfies these needs and provides other related advantages.

SUMMARY OF THE INVENTION

The present invention resides in a device useful in shunt systems for controlling the flow of fluids from one part of the human body to another, which device is constructed substantially of non-metallic materials which prevent adhesion of one part to another, thereby providing trouble-free and reliable operation of the device. Moreover, the apparatus of the present invention is relatively inexpensive to manufacture, and can be easily modified to provide a variety of pressure/flow characteristics.

The accompanying drawings illustrate two embodiments of the present invention which are each constructed to include a relatively rigid, unitized molded plastic base having apertures through which the fluid must flow, and a resilient membrane, molded of a non-metallic material different from the material of the plastic base, which covers the apertures through the base on the downstream side of the base. The resilient membrane is normally biased to prevent flow through the valve, but will open to permit flow through the valve when the pressure upstream of the valve exceeds the pressure downstream of the valve by a predetermined amount.

More specifically, the base separates an inlet chamber covered by a resilient dome from an outlet chamber, and the apertures through the base permit flow from the inlet chamber to the outlet chamber. To permit connection of the valve of the present invention to a conduit of a drainage system, an inlet connector and an outlet connector are integrally molded with a base plate to form the unitized base, and the inlet and outlet connectors are in open communication with the inlet chamber and the outlet chamber, respectively. The resilient membrane is secured to the relatively rigid base by a central support and the membrane overlies the apertures through the base on the outlet chamber side of the base.

A variety of pressure/flow characteristics can be provided by the flow control valve of the present invention by providing such valves with different resilient membranes of varying thicknesses. The resistance to flow through the valves increases with an increase in membrane thickness.

In order to provide the desired resistance to adhesion between the plastic base and the resilient membrane, particularly during storage of the valve, the unitized base is preferably formed of a polypropylene material and the membrane is preferably formed of a silicone elastomer material. Further, the resilient dome which cooperates with the base to form the inlet chamber is also preferably molded of a silicone elastomer material.

A radiopaque indicator in the form of an arrow and preferably situated on the dome is provided to permit X-ray identification of the proximal-to-distal flow path of the device. Similarly, a radiopaque dot code can be generally colocated with the arrow to permit post-operative identification of the pressure/flow rating of the valve by X-ray photography. Furthermore, radiopaque markers are located on the connectors to allow verification of a valve to drain disconnect, by X-ray, if radiopaque surgical tubing separates from the valve after implantation of the system in the body.

Additionally, if desired, the valve of this invention can be constructed to include integral flow occluders. The occluders are located adjacent the inlet and outlet connectors, and are operated by precutaneous finger pressure to allow selective proximal and distal flushing of the device.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

FIG. 3 is a perspective view similar to FIG. 1, illustrating an alternate embodiment of the flow control valve of the present invention;

FIG. 4 is an elevational, sectional view taken generally along the line 4—4 of FIG. 3, including arrows indicating the proximal-to-distal flow path; and FIG. 5 is an elevational, sectional view similar to FIG. 4, illustrating one method of flushing the device in the proximal direction.

DETAILED DESCRIPTION

Figure 1:
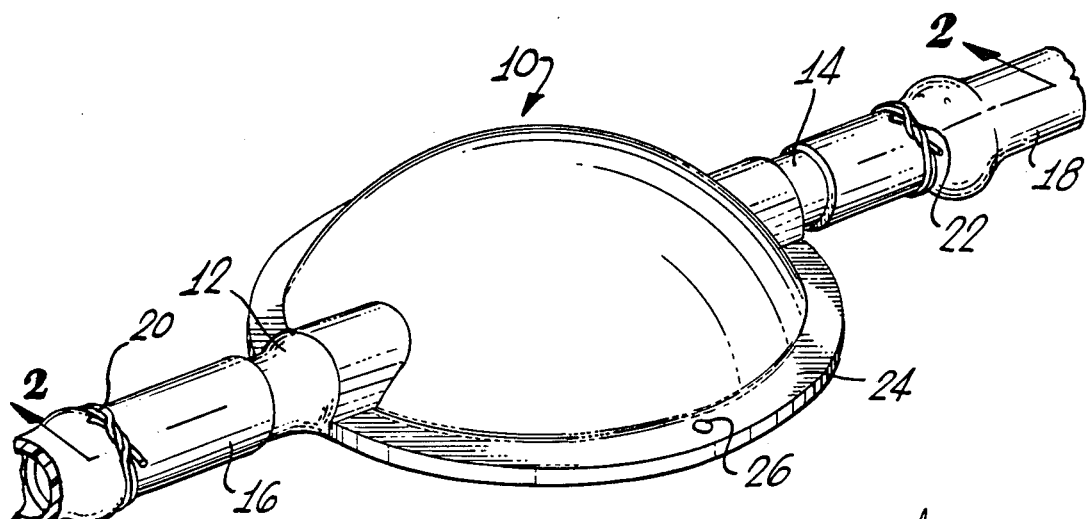
FIG. 1 is a perspective view of the flow control valve of the present invention shown connected to surgical tubing, the tubes being shown in fragmentary form.
Figure 2:
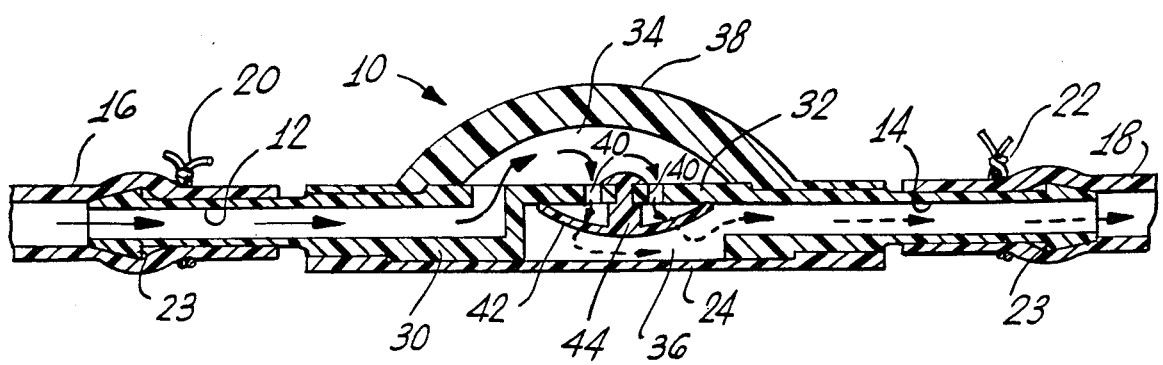
FIG. 2 is an elevational, sectional view of the flow control valve of the present invention, taken substantially along line 2—2 of FIG. 1, and including arrows indicating the direction of fluid flow through the valve.

As shown in the drawings for purposes of illustration, the present invention is concerned with an improved flow control valve, generally designated in FIGS. 1 and 2 by the reference number 10 and in FIGS. 3 through 5 by the reference number 110. These improved flow control valves 10 and 110 are intended for use in a surgically implanted shunt system for draining fluid from one portion of the human body to another. In order to connect, for example, the valve 10 in such a system, the valve includes and inlet connector 12 and an outlet connector 14 which each receive one end of a piece of surgical tubing, illustrated in FIG. 1 as an inlet tube 16 and an outlet tube 18. The tubes 16 and 18 slide over the connectors 12 and 14, and each is secured to its respective connector by a single ligature 20 and 22. The ligatures are preferably secured around the tubing just inside of an annular ridge 23 formed near the end of each connector (FIG. 2).

When the valve 10 is used in a drainage system intended for treatment of hydrocephalus, the inlet tube 16 connects to a proximal catheter (not shown) which is inserted through the skull into a brain ventricle containing cerebrospinal fluid under pressure. The outlet tube 18 connects to a distal catheter (not shown) which serves to discharge cerebrospinal fluid into, for example, the atrium portion of a patient's heart. Ordinarily, a valve 10 will be surgically implanted on the patient's skull with a flap of skin overlying the valve. To facilitate holding the valve in its desired position after implantation, a generally flexible mounting plate 24 of the valve can be provided with one or more suture holes 26.

While two preferred forms of the invention are illustrated in the accompanying drawings, it is to be understood that each embodiment is the functional equivalent of the other. The valve 110 of the invention shown in FIGS. 3 through 5 simply illustrates an alternate valve design and additional features which can be incorporated into the valve 10 illustrated in FIGS. 1 and 2. Both illustrated embodiments of the present invention provide a highly reliable valve designed to prevent valve seat deformation and membrane to seat sticking. The flow control valve of the present invention is inexpensive to produce and designed to facilitate implantation by eliminating components to be connected or adjusted other than the surgical tubing of the shunt system. Also, the use of metal as a functional component of the improved valve has been eliminated.

In accordance with the present invention, and as illustrated with respect to the first embodiment in FIGS. 1 and 2, the valve 10 is constructed to include a relatively rigid, unitized molded plastic base 30 which is formed integrally with the inlet and outlet connectors 12 and 14 (FIG. 2). The base 30 includes a generally horizontal plate 32 which separates an inlet chamber 34 from an outlet chamber 36 in the valve 10.

The inlet chamber 34 is defined generally by the top of the plate 32 and a resilient dome 38 secured to the top of the base 30. The outlet chamber 36 is defined generally by the bottom of the plate 32 and the mounting plate 24. It will be noted that the inlet connector 12 is in open communication with the inlet chamber 34, and the outlet connector 14 is in open communication with the outlet chamber 36. To permit fluid to flow through the valve 10, one or more apertures 40 are provided through the plate 32.

The flow control valve 10 is arranged for controlling the flow of cerebrospinal fluid out of a brain ventricle and preventing backflow of fluid into the brain ventricle by the provision of a resilient non-metallic membrane 42. The membrane 42 is molded of a synthetic polymer material different from the material of the relatively rigid plastic base 30, and is secured to the base in a manner covering the apertures 40 on the outlet chamber side of the base. The resilient membrane 42 is normally biased to close communication from the inlet chamber 34 to the outlet chamber 36, but will open to permit flow (as indicated by the arrows in FIG. 2) when the pressure in the inlet chamber exceeds the pressure in the outlet chamber by a predetermined amount. Moreover, should the pressure in the outlet chamber 36 ever exceed the pressure in the inlet chamber 34, tending to cause flow in reverse direction through the valve 10, the membrane 42 will seal tightly against the plate 32, sealing the apertures 40 and preventing any such reverse flow.

More specifically, the base 30 of the present invention is preferably formed of a polypropylene material, and the membrane 42 is formed of an elastomer material, preferably a silicone elastomer material. Both the polypropylene and elastomer materials have been shown to produce an acceptable level of tissue reaction, and it has been discovered that the use of this particular duality of materials, in contrast to the use of only a single material by the prior art, markedly decreases the chance of the membrane 42 adhering to the base 30, which would clog the drain passage and defeat the whole purpose of the valve 10. Further, the valve of this invention is relatively inexpensive to manufacture, is trouble-free and reliable in use, and can be easily modified to produce a variety of pressure/flow characteristics.

An added advantage of using these particular materials is the avoidance of the negative effect of metal components, due to radiation scatter or "sunburst effect", on films taken by, for example, computerized axial tomography (CAT) scanning equipment. This type of scanning frequently accompanies the use of surgically implanted flow control valves, and the absence or limitation of metal in the area scanned will permit more accurate and complete results to be gathered from CAT scanning.

The membrane 42 has an arch-shape, as for example a section of a sphere, and contacts the lower side of the plate 32 generally along the outer edges of the membrane in a manner surrounding the apertures 40. The membrane 42 is secured to the plate 32 by an upstanding central support 44 which is received in a mounting aperture in the plate and fixed thereto by an interference fit and use of an adhesive, or any other suitable means.

Since the valve 10 of the present invention is primarily designed to provide controlled resistance to cerebrospinal fluid flow from a brain ventricle to an atrium portion of the patient's heart, it will be appreciated that a doctor must be able to select a valve having the particular pressure/flow characteristics desired for each individual application. That is, a valve which permits flow at a relatively low pressure differential may not be suitable where the maintenance of a higher pressure differential is indicated. Toward this end, in order to provide a variety of valves having different pressure/flow characteristics, the valve 10 can be provided with a thick membrane 42 or a relatively thin membrane 42. Resistance to flow increases with the increase in membrane thickness.

The resilient dome 38 is also preferably molded of a silicone elastomer material, and is designed to permit injection into the drainage system by a hypodermic needle through the dome. Further, the dome 38 is sufficiently resilient to be deformed downwardly by external finger pressure. In this way, the flow control valve 10 can be flushed manually in either the proximal or distal direction.

To flush the control valve 10 in the proximal direction, the outlet tube 18 can be occluded by finger pressure, and the dome 38 pressed downwardly as described above. The occlusion of the outlet tube 18 prevents any flow from the valve in the distal direction, and the depression of the dome 38 will therefore cause flushing of the fluid in the valve in the proximal direction. Similarly, by occluding the inlet tube 16 and depressing the dome 38, fluid in the inlet chamber 34 will be forced through the apertures 40, past the membrane 42 and into the outlet tube 18.

From the foregoing, it will be appreciated that the valve 10 of the present invention provides a device by which the flow of cerebrospinal fluid out of a brain ventricle can be controlled while preventing the backflow of fluid into the brain ventricle, and by which the chance of the valve clogging the drain passage can be greatly decreased. Further, the valve 10 can be fabricated conveniently and economically, is trouble-free and reliable in use, and can be easily adapted to provide a variety of pressure/flow characteristics.

These foregoing features are also provided and enhanced in an alternate embodiment of the invention, illustrated in FIGS. 3 through 5, wherein functionally equivalent components common to both embodiments are referred to in the drawings by corresponding reference numbers increased by 100. Generally, the valve 110 is similar to the valve 10 of the first embodiment in that it is constructed to include a relatively rigid, utilized molded plastic base 130 which is formed integrally with inlet and outlet connectors 112 and 114. As was the case with the previously described valve 10, the inlet and outlet connectors 112 and 114 each receive one end of a piece of surgical tubing 116 and 118 which slide over the connectors to be secured to their respective connector by a single ligature 120 and 122. The ligatures are preferably secured around the tubing just inside of an annular ridge 123 formed near the end of each connector.

The valve 110 was designed for use with patients where a smaller, low-profile shape is indicated, such as, for example, in pediatric and geriatric applications requiring subcutaneous implantation.

The base 130 includes a body plate 132 which, in part, separates an inlet chamber 134 from an outlet chamber 136 in the valve 110. The inlet chamber 134 is defined generally by the upper surface of the plate 132 and a resilient dome 138 secured to the top of the base 130. The outlet chamber 136 is defined generally by a void or chamber formed within the base 130 and situated generally adjacent a lower side of the plate 132. It will be noted that the inlet connector 112 is in open communication with the inlet chamber 134, and the outlet connector 114 is in open communication with the outlet chamber 136. To permit fluid to flow through the valve 110, one or more apertures 140 are provided through the plate 132 between the inlet chamber 134 and the outlet chamber 136. Additionally, a generally flexible mounting pad 124 can be provided with one or more suture holes (not shown) and attached generally along the underside of the base 130 to facilitate holding the valve 110 in its desired position after implantation.

The flow control valve 110 is arranged for controlling the flow of cerebrospinal fluid out of a brain ventricle and preventing backflow of fluid into the brain ventricle by the provision of a resilient non-metallic membrane 142 which is very similar to the membrane 42 of the first embodiment. This membrane 142 is molded of a synthetic polymer material different from the material of the relatively rigid plastic base 130, and is secured to the base in a manner covering the apertures 140 on the outlet chamber side of the base. The resilient membrane 142 is normally biased to close communication from the inlet chamber 134 to the outlet chamber 136, but will open to permit flow (as indicated by the arrows in FIG. 4) when the pressure in the inlet chamber exceeds the pressure in the outlet chamber by a predetermined amount. Moreover, should the pressure in the outlet chamber 136 ever exceed the pressure in the inlet chamber 134, tending to cause flow in the reverse direction through the valve 110, the membrane 142 will seal tightly against the plate 132, sealing the apertures 140 and preventing any such reverse flow.

More specifically, the relatively rigid molded plastic base 130 of the present invention is preferably formed of a polypropylene material, and the membrane 142 is formed of an elastomer material, preferably a silicone elastomer material. The membrane 142 has an arch-shape, as for example, a section of a sphere, and contacts the lower side of the plate 132 generally along the outer edges of the membrane in a manner surrounding the apertures 140. The membrane 142 is secured to the plate 132 by an upstanding central support 144 which is received in a mounting aperture in the plate and fixed thereto by an interference fit and the use of an adhesive, or any other suitable means. Also, as described above in connection withthe valve 10, the valve 110 can be provided with a thick membrane 142 or a relatively thin membrane 142.

The resilient dome 138 is also preferably molded of a silicone elastomer material, and is designed to permit injection into the drainage system by a hypodermic needle through the dome. The construction of the base 130 and the dome 138 allows a physician to feel where the needle is during injection. Also, the rigidness of the base 130 prevents the needle from inadvertently passing through the valve 110 and damaging the resilient membrane 142. Further, the dome 138 is sufficiently resilient to be deformed downwardly by external finger pressure. In this way, the flow control valve 110 can be flushed manually in either the proximal or distal direction. Such a feature is desireable to facilitate drainage flow occlusion checks and the administration of medication to the patient.

One of the most noticeable differences between the valve 10 of FIGS. 1 and 2 and the valve 110 of FIGS. 3 through 5 is the shape of the domes 38 and 138. Specifically, the dome 138 includes two wings 146 and 148 having generally flat upper and lower surfaces. These wings 146 and 148 are resilient and deformable to provide a covering over adjacent flat surfaces 150 and 152, respectively, of the plate. The wing 146 is situated over the first flat surface 150 in a manner permitting fluid to flow from the inlet connector 112 through a port 154 situated on the first flat surface, and into the inlet chamber 134. Similarly, the wing 148 is situated over the second flat surface 152 in a manner permitting fluid to flow from the inlet chamber 134 over the second flat surface and through the apertures 140 to be received into the outlet chamber 136.

The wings 146 and 148 interact with their adjacent flat surfaces 150 and 152 to releasably and selectively occlude the fluid passageway through the valve 110 (FIG. 5). For example, to flush the control valve 110 in the proximal direction, the wing 148 can be pressed downwardly so that it contacts the second flat surface 152 to occlude the apertures 140. Next, the dome 138 is pressed downwardly as described above. The occlusion of the apertures 140 prevents any flow from the valve 110 in the distal direction, and the depression of the dome 138 will therefore cause flushing of the fluid in the valve in the proximal direction. Similarly, by pressing downwardly on the wing 146 to occlude the port 154 and then depressing the dome 138, fluid in the inlet chamber 134 will be forced through the apertures 140, past the membrane 142 and into the outlet tube 118. In either case, if there is noticeable resistance to dome 138 compression, the catheter to be flushed may be occluded.

On the upper surface of the dome 138, and specifically over the wing 148, a radiopaque tantalum-impregnated silicone elastomer arrow 156 is situated to designate the proximal-to-distal flow path of the valve 110. The provision of such a radiopaque indicator in the form of the arrow 156 permits X-ray identification of the proximal-to-distal flow path when the device is in place under the skin of the patient. Similarly, a radiopaque tantalum-impregnated silicone elastomer dot code 158 is generally colocated with the arrow 156 to permit post-operative identification of the pressure/-flow rating of the valve 110 by X-ray photography. An example of a useful code would be to utilize one dot to indicate a low pressure valve, two dots to indicate a medium pressure valve, and three dots to indicate a high pressure valve. The dot code for a high pressure valve is shown in FIG. 3.

Furthermore, radiopaque barium sulfate-impregnated markets 160 and 162 have been provided which wrap around a portion of the connectors 112 and 114. These radiopaque markers 160 and 162 provide means whereby a physician can detect the separation of the surgical tubing 116 and 118 from the valve 110 after implantation. Such valve/tubing disconnect is readily detectable in a shunt system through the use of X-ray photography when radiopaque surgical tubing is connected to the valve 110.

From the foregoing, it will be appreciated that the valves 10 and 110 of the present invention provide a device by which the flow of cerebrospinal fluid out of a brain ventricle can be controlled while preventing the backflow of fluid into the brain ventricle, and by which the chance of valve clogging the drain passage can be greatly decreased. Both valves 10 and 110 can be fabricated conveniently and economically, are trouble free and reliable in use, provide convenient proximal and distal flushing of the shunt system, and can be easily adapted to provide a variety of pressure/flow characteristics. Further, the inclusion of radiopaque indicators and markers provides the surgeon means for ascertaining specific information about the device itself and the functioning of the shunt system which would otherwise be unavailable without additional surgery.

While two particular forms of the invention have been illustrated and described, it will be apparent that various modifications can be made without departing from the spirit and scope of the invention. Accordingly, it is not intended that the invention be limited, except as by the appended claims.

We claim:

1. A surgically implantable flow control valve for controlling the flow of fluid from one portion of the human body to another, said valve comprising:

a substantially rigid polypropylene base of utilized construction including a plate having an inlet surface and an outlet surface, a tubular inlet connector integral with said plate, and a tubular outlet connector integral with said plate;

an inlet passageway through said base, said inlet passageway originating at an open end of said inlet connector and terminating at an inlet port situated on said inlet surface of said plate;

an outlet passageway through said base, said outlet passageway originating at an outlet port adjacent said outlet surface and terminating at an open end of said outlet connector;

a resilient dome substantially overlying said base and said inlet port, said dome having an arch-shape similar to one-half of a sphere, the inner surface of said dome being smooth and forming a seal against an upper surface of said base to create an inlet chamber between said dome and said base, said dome being deformable toward said base by external pressure so that the extent of deformation is limited by contact between said dome and said base;

a mounting pad generally underlying said base and interacting with the edges of said dome to substantially encase said base in connection with said dome;

an outlet chamber between said outlet surface and said outlet port;

a plate passageway permitting fluid communication between said inlet chamber and said outlet chamber;

a flow control member including a central support and a resilient membrane, said central support being securely attached to said base and extending therefrom into said outlet chamber to support said membrane, said membrane being generally arch-shaped and resiliently biased to normally contact said outlet surface generally along the outer edges of said membrane in a manner surrounding said plate passageway and forming a releasable seal between said outlet surface and the outer edges of said membrane, said outlet surface being sufficiently rigid to maintain a proper valve seat for the outer edges of said membrane despite pressure applied to said inlet surface caused by contact of said dome with said inlet surface when said dome is fully deformed, said membrane being formed of an elastomer material to prevent sticking with said polypropylene base;

means for occluding said inlet port in a manner permitting deformation of said dome to cause fluid contained in said inlet chamber to pass through said plate passageway into said outlet chamber and finally through said outlet passageway, said inlet port occluding means useful for flushing said valve in a distal direction;

means for occluding said plate passageway in a manner permitting deformation of said dome to cause fluid contained in said inlet chamber to pass through said inlet port into said inlet passageway, said plate passageway occluding means useful for flushing said valve in a proximal direction;

a radiopaque indicator situated on the upper surface of said dome, said indicator being X-ray detectable after implantation of said valve in the body for indicating the proximal-to-distal flow path through said valve;

an inlet radiopaque marker generally encircling a portion of said inlet connector; and an outlet radiopaque marker generally encircling a portion of said outlet connector.

2. A valve as recited in claim 1, including means for determining the pressure/flow characteristics of said valve by X-ray photography/after implantation of said valve in the body.

3. A surgically implantable flow control valve for controlling the flow of fluid from one portion of the human body to another, said valve comprising:
   an inlet;
   an outlet;
   a relatively rigid base forming a wall separating said inlet from said outlet;
   an aperture through said wall for permitting flow of the fluid through said valve from said inlet to said outlet;
   a flow control member, including a central support and a resilient membrane, said central support being securely attached to said wall adjacent said aperture and extending therefrom on the outlet side of said wall to support said membrane, said membrane being generally arch-shaped and resiliently biased to normally contact the outlet side of said wall generally along the outer edges of said membrane in a manner surrounding said aperture and forming a releasable seal between the outlet side of said wall and the outer edges of said membrane;
   means for indicating the proximal-to-distal flow path through said valve, said indicating means being X-ray detectable after implantation of said valve in the body;
   an inlet radiopaque marker generally situated adjacent a portion of said inlet; and
   an outlet radiopaque marker generally situated adjacent a portion of said outlet.

4. A valve as recited in claim 3, including means for determining the pressure/flow characteristics of said valve by X-ray photography after implantation of said valve in the body.

5. A valve is recited in claim 3, wherein said membrane is formed of an elastomer material and said base is formed of a polypropylene material.

6. A valve as recited in claim 3, wherein said base includes a rigid plate which provides a planar valve seat to facilitate the formation of a releasable seal between the outer edges of said membrane and said plate, said plate having an inlet surface in communication with said inlet and an outlet surface in communication with said outlet.

7. A valve as recited in claim 6, including a flexible encasement generally surrounding said base, said encasement being deformable toward said inlet surface by external pressure primarily to facilitate manual flushing of said valve.

8. A valve as recited in claim 7, wherein said central support carries said membrane adjacent said outlet surface in a manner permitting deformation of said encasement without affecting the normal operation of said membrane.

9. A valve as recited in claim 3, further including a resilient dome secured to said base over the inlet side of said wall to form an inlet chamber in communication with said inlet, said dome being deformable toward said wall by external pressure, and said indicating means being situated on the upper surface of said dome.

10. A valve as recited in claim 9, wherein said dome includes a first wing and a second wing situated over said base, said first wing providing means for occluding said inlet in a manner permitting deformation of said dome to cause fluid contained in said inlet chamber to pass through said aperture into said outlet, said second wing providing means for occluding said aperture in a manner permitting deformation of said dome to cause fluid contained in said inlet chamber to be expelled from said valve through said inlet.

11. A surgically implantable flow control valve for controlling the flow of fluid from one portion of the human body to another, said valve comprising:
   an inlet including an inlet chamber;
   an outlet including and outlet chamber;
   a base of unitized construction including a rigid plate which resists deformation, said plate having an inlet surface in communication with said inlet chamber and an outlet surface in communication with said outlet chamber;
   an aperture through said plate for permitting flow of the fluid through said valve from said inlet chamber to said outlet chamber;
   a flow control member including a central support and a resilient membrane, said central support being securely attached to said outlet surface and extending therefrom to support said resilient membrane, said resilient membrane being generally arch-shaped so that the outer edges of said membrane normally contact said outlet surface in a manner surrounding said aperture;

means for occluding said inlet; and means for occluding said aperture in a manner preventing fluid communication between said inlet chamber and said outlet chamnber.

12. A valve as recited in claim 11, further including a resilient dome secured to said base over a portion of said inlet to form said inlet chamber, said dome being deformable toward said base by external pressure and having a radiopaque indicator situated on the upper surface of said dome, said indicator being X-ray detectable after implantation of said valve in the body for indicating the proximal-to-distal flow path through said valve.

13. A valve as recited in claim 12, including means for determining the pressure/flow characteristics of said valve by X-ray photography after implantation of said valve in the body.

14. A valve as recited in claim 11, further including an inlet radiopaque marker generally encircling a portion of said inlet and an outlet radiopaque marker generally encircling a portion of said outlet.

15. A valve as recited in claim 11, wherein said member is molded of a non-metallic synthetic polymer material different from the material of said base.

16. A valve as recited in claim 15, wherein said base is formed of a polypropylene material and said member is formed of an elastomer material.

17. A surgically implantable flow control valve for controlling the flow of fluid from one portion of the human body to another, said valve comprising:

an inlet;

an outlet;

a base including a plate having an inlet surface in communication with said inlet and an outlet surface in communication with said outlet;

an aperture through said plate permitting said inlet to communicate with said outlet;

a flow control member including a central support and a resilient membrane, said central supporting being securely attached to said outlet surface and extending therefrom to supporting said resilient membrane, said resilient membrane being generally arch-shaped so that the outer edges of said membrane normally contact said outlet surface in a manner surrounding said aperture;

an inlet radiopaque marker situated adjacent a portion of said inlet; and an outlet radiopaque marker situated ajacent a portion of said outlet.

18. A valve as recited in claim 17, including a resilient dome secured to said base over said inlet surface, said dome cooperating with said inlet surface to form an inlet chamber in communication with said inlet, said dome being deformable toward said inlet surface by external pressure.

19. A valve is recited in claim 18, further including a radiopaque indicator situated on the upper surface of said dome, said indicator being X-ray detectable after implantation of said valve in the body for indicating the proximal-to-distal flow path through said valve.

20. A valve as recited in claim 17, wherein said membrane is carried adjacent said outlet surface in a manner permitting deformation of said dome without affecting the normal operation of said membrane.

21. A valve as recited in claim 17, including means for determining the pressure/flow characteristics of said valve by X-ray photography after implantation of said valve in the body.

22. A valve as recited in claim 17, further including means for occluding said inlet in a manner permitting deformation of said dome to cause fluid contained in said inlet chamber to pass through said aperture into said outlet, said inlet occluding means useful for flushing said valve in a distal direction.

23. A valve as recited in claim 17, further including means for occluding said aperture in a manner permitting deformation of said dome to cause fluid contained in said inlet chamber to pass through said inlet, said aperture occluding means useful for flushing said valve in a proximal direction.

24. A surgically implantable flow control valve for controlling the flow of fluid from one portion of the human body to another, said valve comprising:

a base of unitized construction, including a substantially rigid plate having an inlet surface and an outlet surface, an inlet connector integral with said plate, and an outlet connector integral with said plate, said inlet surface of said plate having a first surface and a second surface;

an inlet passageway through said base, said inlet passageway originating at an open end of said inlet connector and terminating at an inlet port on said first surface;

an outlet passageway through said base, said outlet passageway originating at an outlet port adjacent said outlet surface and terminating at an open end of said outlet connector;

an inlet chamber adjacent said inlet surface, said inlet chamber communicating with said inlet passageway at said inlet port;

an outlet chamber adjacent said outlet surface, said outlet chamber communicating with said outlet passageway at said outlet port;

a plate passageway permitting fluid communication between said inlet chamber and said outlet chamber;

a flow control member including a central support and a resilient membrane, said central support being securely attached to said base plate and extending therefrom into said outlet chamber to support said membrane, said membrane being generally arch-shaped and resiliently biased to normally contact said outlet surface generally along the outer edges of said membrane in a manner surrounding said plate passageway; and means for indicating the proximal-to-distal flow path through said valve, said indicating means being X-ray detectable after implantation of said valve in the body.

25. A valve as recited in claim 24, including a resilient dome secured to said base generally over said inlet surface, said dome cooperating with said inlet surface to form said inlet chamber, said dome being deformable toward said inlet surface by external pressure for primarily causing manual flushing of said valve, said indicating means being situated generally on the upper surface of said dome.

26. A valve as recited in claim 25, including means for occluding said inlet port in a manner permitting deformation of said dome to cause fluid contained in said inlet chamber to pass through said plate passageway into said outlet chamber and finally through said outlet passageway.

27. A valve as recited in claim 26, wherein a first portion of said dome resiliently covers said first surface in a manner permitting said first portion of said dome to interact with said first surface to occlude said inlet port.

28. A valve as recited in claim 25, including means for occluding said plate passageway in a manner permitting deformation of said dome to cause fluid contained in said inlet chamber to pass through said inlet port into said inlet passageway.

29. A valve as recited in claim 28, wherein a second portion of said dome covers said second surface in a manner permitting said second portion of said dome to be resiliently pressed against said second surface to occlude said plate passageway.

30. A valve as recited in claim 24, including an inlet radiopaque marker situated on said inlet connector near said open end of said inlet connector.

31. A valve as recited in claim 24, including an oulet radiopaque marker situated on said outlet connector near said open end of said outlet connector.

32. A valve as recited in claim 24, including means for determining the pressure/flow characteristics of said valve by X-ray photography after implantation of said valve in the body.

33. A surgically implantable flow control valve for controlling the flow of fluid from one portion of the human body to another, said valve comprising:
   an inlet;
   an outlet;
   a base including a plate having an inlet surface in communication with said inlet and an outlet surface in communication with said outlet;
   an aperture through said plate permitting said inlet to communicate with said outlet; and
   a flow control member including a central support and a resilient membrane, said central support being securely attached to said outlet surface and extending therefrom to support said resilient membrane, said resilient membrane being generally arch-shaped so that the outer edges of said membrane contact said outlet surface in a manner surrounding said aperture.

34. A valve as recited in claim 33 wherein said membrane is molded of a non-metallic synthetic polymer material different from the material of said base.

35. A valve as recited in claim 34 wherein said base is formed of a polypropylene material.

36. A valve as recited in claim 35 wherein said membrane is formed of an elastomer material.

37. A valve as recited in claim 33 including a flexible encasement generally surrounding said base.

38. A valve as recited in claim 37 wherein said encasement is deformable toward said inlet surface by external pressure primarily to facilitate manual flushing of said valve.

39. A valve as recited in claim 38 wherein said central support holds said membrane adjacent said outlet surface in a manner permitting full deformation of said encasement toward said inlet surface without affecting the seal between the outer edges of said membrane and said plate.

40. A valve as recited in claim 38 wherein said base is sufficiently rigid to maintain a proper valve seat for said membrane on said outlet surface despite external pressure applied to said inlet surface when said encasement is fully deformed.

41. A valve as recited in claim 33 further including a resilient dome secured to said base over the inlet side of said plate to form an inlet chamber in communication with said inlet, said dome being deformable toward said plate by external pressure.

42. A valve as recited in claim 11, including an inlet connector forming a portion of said inlet and an outlet connector forming a portion of said outlet, said inlet and outlet connectors being integrally formed with said base.

43. A valve as recited in claim 17, wherein said base is formed of a polypropylene material and said flow control member is formed of a non-metallic synthetic polymer material.

* * * * *

UNITED STATES PATENT AND TRADEMARK OFFICE
CERTIFICATE OF CORRECTION

PATENT NO. : 4,560,375

DATED : December 24, 1985

INVENTOR(S) : Rudolf R. Schulte, et al.

It is certified that error appears in the above-identified patent and that said Letters Patent is hereby corrected as shown below:

In Column 3, line 49, please delete the first "and" and insert therefor --an--.

In Column 6, lines 5 and 6, please delete the word "utilized" and insert therefor --unitized--.

In Column 7, line 5, please delete the word "withthe" and insert therefor -- with the--.

In Column 8, line 8, please delete the word "markets" and insert therefor --markers--.

In Column 8, line 44, please delete the word "utilized" and insert therefor --unitized--.

In Column 10, line 17, please delete the word "is" and insert therefor --as--.

In Column 11, line 44, please delete the word "supporting" and insert therefor --support--.

In Column 11, line 47, please delete the word "supporting" and insert therefor --support--.

UNITED STATES PATENT AND TRADEMARK OFFICE
CERTIFICATE OF CORRECTION

PATENT NO. : 4,560,375
DATED : December 24, 1985
INVENTOR(S) : Rudolf R. Schulte, et al.

It is certified that error appears in the above-identified patent and that said Letters Patent are hereby corrected as shown below:

In Column 11, line 54, please delete the word "ajacent" and insert therefor --adjacent--.

In Column 11, line 62, please delete the word "is" and insert therefor --as--.

Signed and Sealed this

Eighteenth Day of March 1986

[SEAL]

Attest:

DONALD J. QUIGG

Attesting Officer

Commissioner of Patents and Trademarks